United States Patent
Ellman et al.

(10) Patent No.: US 6,387,093 B1
(45) Date of Patent: May 14, 2002

(54) RADIO FREQUENCY TONGUE BASE ELECTRODE

(76) Inventors: Alan G. Ellman; Jon C. Garito, both of 1135 Railroad Ave., Hewlett, NY (US) 11557

( * ) Notice: Subject to any disclaimer, the term of this patent is extended or adjusted under 35 U.S.C. 154(b) by 0 days.

(21) Appl. No.: 09/442,316

(22) Filed: Nov. 22, 1999

Related U.S. Application Data

(63) Continuation-in-part of application No. 09/303,839, filed on May 3, 1999, now Pat. No. 6,231,571.

(51) Int. Cl.[7] ................................................ A61B 18/18
(52) U.S. Cl. ............................. 606/39; 606/41; 606/45; 607/99; 607/115; 128/898
(58) Field of Search ................................ 606/32, 39, 41, 606/45; 607/96, 98, 99, 115, 116, 134; 128/898

(56) References Cited

U.S. PATENT DOCUMENTS

| | | |
|---|---|---|
| 5,505,728 A | 4/1996 | Ellman et al. |
| 5,571,101 A | 11/1996 | Ellman et al. |
| 5,755,716 A | 5/1998 | Garito et al. |
| 5,993,447 A * | 11/1999 | Blewett et al. ............... 606/41 |
| 6,245,068 B1 * | 6/2001 | Olson et al. ................. 606/41 |

* cited by examiner

Primary Examiner—R. Kearney

(57) ABSTRACT

An electrosurgical electrode comprises a generally L-shaped metal member comprising an electrically-insulated, generally straight shank part for mounting in a standard electrosurgical handpiece, and a generally curved part divided into first, second, third, and fourth sections, the second, third, and fourth of which are electrically-insulating and the first of which is bare and terminates in a pointed end. The second and third sections are covered with a thin electrically-insulating coating, whereas the fourth section, closest to the shank, is covered with a thicker electrically-insulating coating. The first, second, and third sections are dimensioned and constructed so as to enable the surgeon to know fairly precisely the depth of the first section in tissue targeted for radiofrequency thermal ablation. An important application is volumetric shrinkage of tongue base tissue, for example, for treating sleep disordered breathing.

7 Claims, 2 Drawing Sheets

RADIO FREQUENCY TONGUE BASE ELECTRODE

RELATED APPLICATION

U.S. application, Ser. No. 09/303,839, filed May 3, 1999 U.S. Pat. No. 6,231,571, commonly owned, for "Electrosurgical Handpiece For Treating Tissue", of which the present application is a continuation-in-part.

This invention relates to a tongue base electrode for treating sleep disordered breathing with radio frequency energy.

BACKGROUND OF THE INVENTION

Out prior U.S. Pat. No. 5,505,728, whose contents are hereby incorporated by reference, describes a novel electrode and electrosurgical procedure for treating Obstructive Sleep Apnea Syndrome (OSAS) by shaving off superficial thin layers of patient airway obstructing tissue.

Our referenced U.S. application, Ser. No. 09/303,839, whose contents are hereby incorporated by reference, describes apparatus for use in a surgical procedure commonly known as minimally invasive surgery (MIS), for treating, say, a herniated disk to remove undesired regions and to provide controlled heat to shrink the tissue during surgery. The electrode for MIS use is preferably constructed with a flexible end controllable by the surgeon so as to allow the surgeon to manipulate the end as desired during the surgical procedure.

This tissue shrinking concept has recently been extended to the treatment of other disorders. It is known as Radio Frequency Thermal Ablation (RFTA), which uses radio frequency (RF) heating to create targeted tissue ablation resulting in tissue volume reduction. One proposed application, described in a paper published in Kania, Sep. 25, 1999 by Pr. B. Meyer, is for the treatment of OSAS and more generally sleep disordered breathing (SDB). The proposed procedure is to insert an electrode into the tongue base below the uvula and apply RF energy such that resistive heating of the tissue occurs, raising the temperature of the immediately surrounding tissue to a temperature that damages or kills the cells. This produces a small lesion which is later replaced by scar tissue and removed by the body, resulting in the shrinkage or volumetric reduction of the treated tissue. This procedure by reducing the volume of the local tissue may enlarge the airway alleviating SDB.

SUMMARY OF THE INVENTION

The present invention describes a novel electrode that can be used with low voltage, low power electrosurgical apparatus for the purpose of implementing RFTA with a relatively simple, easily learned procedure.

Briefly stated, the novel electrode comprises a generally L-shaped metal member comprising an electrically-insulated, generally straight shank part for mounting in a standard electrosurgical handpiece, and a generally curved needle-shaped part divided into first, second, third, and fourth sections, the second, third, and fourth of which are electrically-insulating and the first of which, the active section, is bare and terminates in a pointed end. The second and third sections are covered with a thin electrically-insulating coating, whereas the fourth section, closest to the shank, is covered with a thicker electrically-insulating coating. The first, second, and third sections are dimensioned and constructed so as to enable the surgeon to know fairly precisely the depth of the active first section in the targeted tissue. In a preferred embodiment, each of the first, second, and third sections are about 1 cm long, and the electrically-insulating coatings on the second and third sections are color-coded differently so they can be visually distinguished so as to enable the surgeon to determine the depth in the tissue of the active first section by the color of the needle-shaped electrode part remaining outside of the tissue.

For completeness' sake, attention is directed to our U.S. Pat. No. 5,755,716, which describes an electrode for treating glaucoma, but this electrode is unsuitable for treating SDB because the electrode has no point capable of penetrating tough tongue base tissue, and one side of the active end is coated, which means that the heat generated is assymetrical about the electrode and will not achieve the results desired. Attention is also directed to our U.S. Pat. No. 5,571,101, which describes an electrode for a DCR procedure, but this electrode is unsuitable for treating SDB because the electrode tip is too short, and does not have 2 separate thin-coated sections following the bare section. Moreover, both patents describe the use of their electrode with conventional high-voltage electrosurgical apparatus for excising or cutting tissue by using current discharges rather than the low-power, low-voltage apparatus needed for RFTA which relies on resistive heating.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described the preferred embodiments of the invention.

DETAILED DESCRIPTION OF THE PREFERRED EMBODIMENTS

The reader is directed to the referenced prior application and paper which will assist in understanding the improvements offered by the present application.

Figure 1:
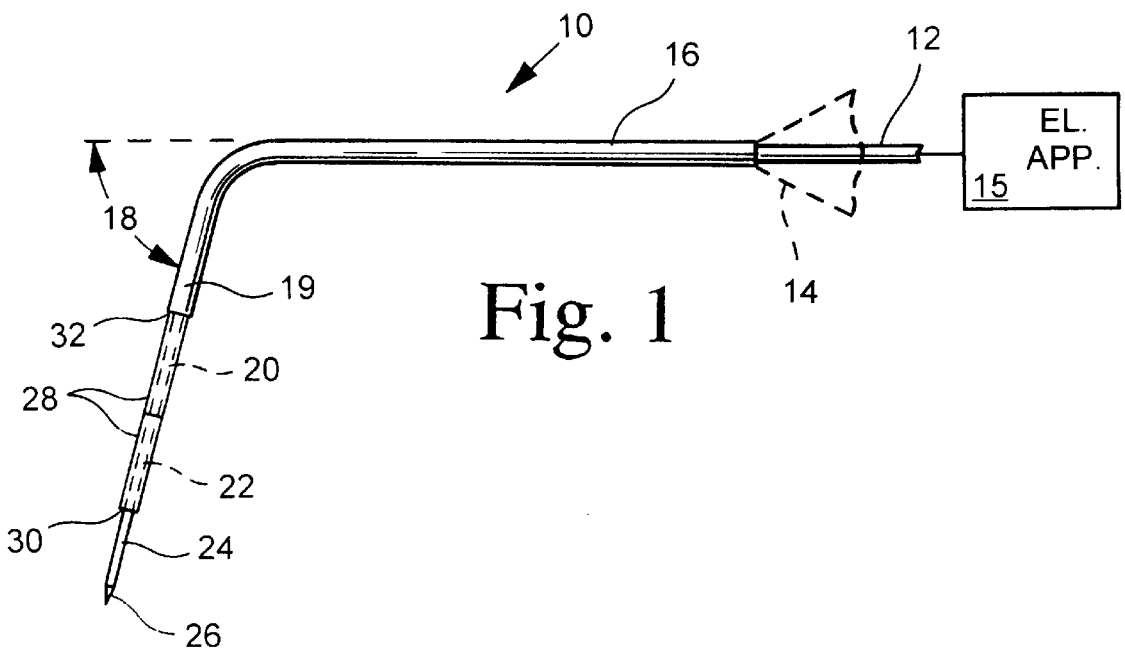
FIG. 1 is a side view of one form of an electrode in accordance with the invention.

As mentioned, low-power, low-voltage electrosurgical apparatus is needed. Such apparatus is available from Ellman International of Hewlett, N.Y. as Model IEC50. The handpiece that can be used is standard, available commercially. It typically comprises (see U.S. Pat. No. 5,571,101) an insulated barrel to be held by the surgeon with a collet type fitting for receiving the bare shank of an electrosurgical electrode. In the preferred embodiment of an electrode according to the invention illustrated in FIG. 1, the electrode 10 comprises preferably, a one piece metal core that is bare at one end 12 which is dimensioned to fit into the collet of the handpiece 14 (shown schematically) whose cable in turn is plugged into the electrosurgical apparatus 15. The straight (horizontal) shank part of the electrode is coated with a thick 16 coating of electrically-insulating material. The thickly-coated part then bends at about a 75° angle 18 to form another straight part 19 which includes an extension of the thickly-coated part which is then followed by a needle-shaped part comprising 2 thinly-coated sections 22, 20 and a bare section 24 with a sharply pointed end 26. The bare section 24, the 2 thinly-coated sections 20, 22, and the straight part 19 have been previously referred to as the first, second, third, and fourth sections, respectively. The thin electrically-insulating coating 28 on the second 24 and third 22 sections forms a first small shoulder 30 where it adjoins the first section 24 and a second shoulder 32 where it adjoins the fourth section 19.

Preferably, the thin coating 28 is formed by fused powdered Teflon having a thickness of about 0.002–0.008 inches, and the thicker coating 16, which is less critical, can be of heat-shrunk plastic tubing. The straight shank section can have an overall length of about 2.0–2.8 inches, and the length of the fourth section 19 can be about 0.6–0.9 inches. The most critical dimensions are the lengths of the first, second, and third sections 24, 22, 20 of the needle. These are preferably of the same length of about 0.8–1.2 cm each, preferably 1 cm. The metal core can be a 0.062 inch brass tube, which is sufficiently stiff and strong that it will withstand excessive flexing and hold its shape when the needle end is pushed into tissue, but yet can still be moderately shaped by the surgeon adjusting the angle 18 if felt necessary. The angle 18, however, preferably is maintained between about 60° and 90°. The point 26 at the bare end must be sufficently sharp so that it can easily penetrate tongue base tissue as deep as necessary during the procedure without causing the electrode to unduly change its shape. The insulation of the thin electrically-insulating coating 28 must be capable of not fracturing during the procedure to avoid RF leakage that could create ulceration, as well as be normally capable of resisting RF leakage when whole, yet must be sufficently smooth so as not to create undue friction between it and the tissue as the electrode penetrates the tissue, and be able to withstand repeated use in puncturing and penetrating tissue. The fused Teflon powder has the necessary attributes to satisfy these requirements. The needle outside diameter must be small enough to enable easy penetration into the tissue yet large enough to withstand the flexing forces involved in the penetration. A size between about 0.04–0.08 inches is suitable. The sharpened end, again for easy penetration, preferably tapers to a sharp point over a distance of about 2–4 mm.

The second and third sections 22 and 20 are differently colored so that they are easily visually distinguished; the third section 20 must be visually distinguishable from the fourth section 19; and the color chosen for the second section 22 must be visually distinguished from the bare metal first section 24. Hence, the surgeon sees a needle-shaped pointed electrode with 3 visually-distinct sections each preferably about 1 cm long followed by a thicker fourth section also preferably of a different color.

The surgical procedure is as follows. Only the steps relative to the invention are recited in broad terms. See FIGS. 2A–2C.

Figure 2A:
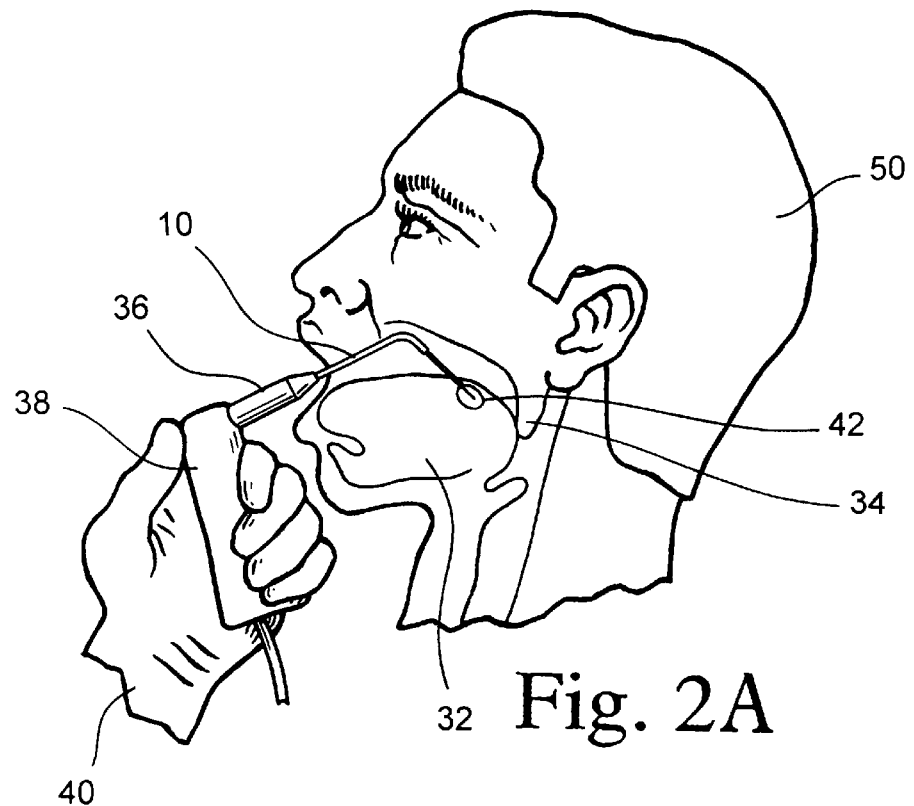
FIGS. 2A, 2B and 2C are schematic perspective views illustrating how the electrode of FIG. 1 can be used to treat SDB by RFTA.
Figure 2B:
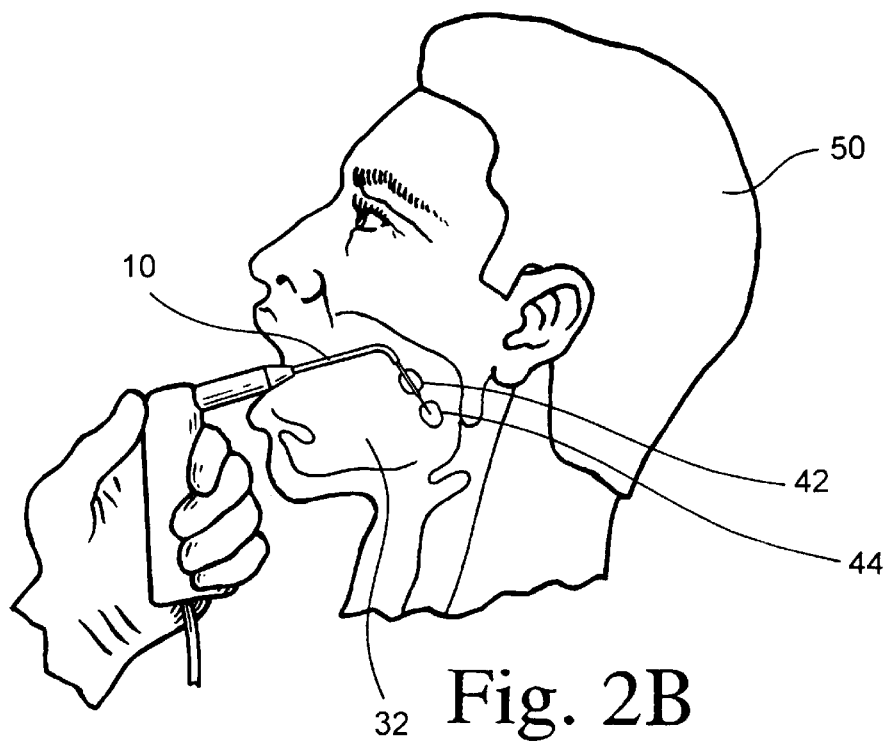

The unipolar handpiece 14 is connected in the usual way to the electrosurgical apparatus 15. FIG. 2A shows a patient 50 with open mouth with the throat airway passing over a tongue 32 leading to the uvula 34. Note that the uvula 34 is close to the tongue possibly obstructing the air flow passage. The electrode handpiece 36 in this case is shaped like a gun handle 38 that can be held in the surgeon's hand 40. The electrode 10 is mounted in the handpiece 36 in the usual way. The surgeon inserts the electrode 10, pointed end 26 first, into the tongue base of the patient, to a depth substantially equal to the length of the first section 24. This is visually obvious as the color of the electrode changes from the first section 24 to the second section 22, and from the second section 22 to the third section 20. The surgeon then activates the electrosurgical apparatus and electrode 10 choosing operating parameters such that relatively low power, low voltage settings of the apparatus are chosen. For the IEC50 instrument, which generates an output power of about 50 watts, a typical power setting of about 3–8 can be used. These values can be determined beforehand using test tissue, typically animal, and measuring the temperature due to resistive heating in the tissue surrounding the tip of the needle after a reasonable ON time of the instrument, say about 8–20 sec. The goal should be a tissue temperature between about 50° and 100° C., at which temperatures the tissue in a first area 42 surrounding the inserted electrode section 24 carbonizes. When the needle electrode 10 is then withdrawn, scar tissue is formed which ultimately becomes absorbed by the body shrinking the tissue volume. This normally will enlarge the throat passageway alleviating the symptoms. In most instances, the tissue shrinkage will have to be increased before a sufficient reduction is accomplished, and the surgeon by examination will be able to judge how much will be needed.

Figure 2C:
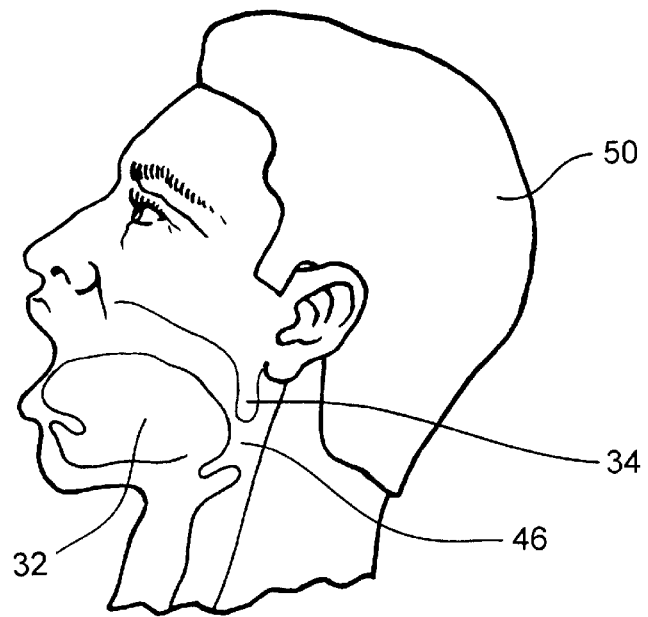

If more shrinkage would be required than can be obtained from a single treatment with the 1 cm penetration, before or after the apparatus has been turned off and while the tissue remains heated or is allowed to cool down if desired, the surgeon (FIG. 2B) presses down on the electrode 10 until it penetrates up to the third section 20, which means that the needle has now penetrated a total of 2 cm. The surgeon now restarts the instrument for another 8–20 sec at the same settings. This time, the resistive heating occurs in a second area 44 around the bare first section 24 now 2 cm deep into the tissue. No heating occurs around the penetrated second section 22, because it is adequately electrically-insulated and no electrosurgical currents flow into the tissue from the second section 22. Thus the depth of the tissue damage is extended further into the tissue. The procedure can be repeated yet a third time by further penetrating the tissue up to the fourth section 19, which will have a different color from the third section 20. Now the needle depth is approximately 3 cm and a deeper region of the tissue is damaged with its subsequent shrinkage. In most cases, penetration up to 3 cm is adequate to accomplish a significant reduction in the tissue volume and concomitant enlargement 46 of the throat passageway. This is illustrated in FIG. 2C.

The color-coded sections of the needle each of the same length means that the surgeon need merely push the needle into the tissue until the next colored section remains outside, and so on, to ensure that each activation of the needle will produce a lesion of approximately 1 cm at a time into the tissue. The simplicity of the procedure is evident. The difference between the tissue shrinkage process and a typical electrosurgical cutting is that, with the latter, the surgeon uses the activated electrode for the shortest time possible while cutting to avoid extensive tissue damage, while, with the tissue shrinkage procedure, the active electrode stays in the tissue a reasonable time at each penetration to ensure that extensive tissue damage will occur, since it is only the damaged tissue that will shrink.

The insulating tube 16 will prevent accidental touching of patient tissue by the electrode sides, so that the electrosurgical curents are localllized to the bare electrode end.

The apparatus used in the procedure preferably generates electrosurgical currents with a frequency of about 2.5–4 M , with 4 MHz preferred. It is found that this frequency range provides a more controlled lesion size for greater reproduciblity. It will also be appreaciated that a higher-powered electrosurgical apparatus can also be used provided that a lower power setting is chosen to keep the power level below about 50 watts. In the preferred example, the apparatus HEMO setting is preferably chosen as it produces a partially-rectified RF waveform for reduced cutting.

While the electrode described has particular utility for shrinking tongue base tissue, it will be appreciated that it may also be of use for shrinking other tissue when such tissue may be causing blockage or obstruction of bodily functions, While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. A procedure for treating sleep disordered breathing, comprising the steps:
    i) providing electrosurgical apparatus connected to an electrosurgical electrode for radiofrequency thermal ablation, said electrosurgical electrode comprising:
        (a) an electrically-conductive member comprising at a first end means for connecting to electrosurgical apparatus and at a second end a pointed tip of a needle-shaped electrode for penetrating tissue,
        (b) said electrically-conductive member comprising, in order from the pointed tip, first, second, third, and fourth adjacent sections,
        (c) said first section being bare so as to allow the passage of electrosurgical currents to the penetrated tissue when the electrosurgical apparatus is activated,
        (d) said second section having a relatively thin electrically-insulating coating so as to prevent the passage of electrosurgical currents to tissue penetrated by the second section when the electrosurgical apparatus is activated,
        (e) said third section having a relatively thin electrically-insulating coating so as to prevent the passage of electrosurgical currents to tissue penetrated by the third section when the electrosurgical apparatus is activated,
        (f) said fourth section having a relatively thick electrically-insulating coating so as to prevent the passage of electrosurgical currents to contacted tissue when the electrosurgical apparatus is activated,
        (g) said first, second, third, and fourth sections being visually distinct from the adjacent section such that a user can determine the depth of penetration in the tissue of the needle-shaped electrode when tissue has been penetrated by examining the sections remaining outside the tissue,
    (ii) penetrating the tissue with the pointed end to a depth equal to the length of the first section using the distinct visual indication of the second section,
    (iii) activating the electrosurgical apparatus to provide at the first section low voltage, low power electrosurgical currents until the tissue adjacent the pointed end is damaged,
    (iv) penetrating the tissue with the pointed end to a depth equal to the length of the first and second sections using the distinct visual indication of the third section,
    (v) activating the electrosurgical apparatus to provide at the first section low voltage, low power electrosurgical currents until the tissue adjacent the deeper pointed end is damaged.

2. The procedure of claim 1, wherein the electrosurgical apparatus generates electrosurgical currents with a frequency of 4 Mhz.

3. The procedure of claim 1, wherein the first, second, third, and fourth sections are visually distinct by reason of differently colored exteriors.

4. The procedure of claim 1, wherein, following step (v):
    (vi) penetrating the tissue with the pointed end to a depth equal to the length of the first, second and third sections using the distinct visual indication of the fourth section;
    (vii) activating the electrosurgical apparatus to provide at the first section low voltage, low power electrosurgical currents until the tissue adjacent the deeper pointed end is damaged.

5. The procedure of claim 1, wherein the first, second, and third sections have substantially the same length.

6. The procedure of claim 5, wherein the first, second, and third sections each have a length of about 1 cm.

7. The procedure of claim 1, wherein the electrosurgical apparatus generates electrosurgical currents at a relatively low-voltage, relatively low-power, and at a frequency in excess of 2.5 MHz.

* * * * *